United States Patent [19]

Masse et al.

[11] Patent Number: 4,728,333

[45] Date of Patent: Mar. 1, 1988

[54] MODULAR PROSTHESIS KIT

[76] Inventors: André A. Masse, 21, rue Brizeux, 35000 Rennes; Christian J. Malet, 14, rue Sarrette, 75014 Paris, both of France

[21] Appl. No.: 848,505

[22] Filed: Apr. 7, 1986

[30] Foreign Application Priority Data

Apr. 5, 1985 [FR] France .................. 85 05348

[51] Int. Cl.⁴ .............................................. A61F 2/32
[52] U.S. Cl. ...................................... 623/23; 623/16; 128/92
[58] Field of Search ...................... 623/16–23; 128/92

[56] References Cited

U.S. PATENT DOCUMENTS

| 4,285,070 | 8/1981 | Averill | 623/20 |
| 4,309,778 | 1/1982 | Buechel et al. | 623/20 |
| 4,340,978 | 7/1982 | Buechel et al. | 623/20 |
| 4,596,580 | 6/1986 | Weill | 623/22 |

FOREIGN PATENT DOCUMENTS

| 0085147 | 8/1983 | European Pat. Off. | 623/23 |
| 1158993 | 9/1979 | France | 128/92 |

Primary Examiner—Richard J. Apley
Assistant Examiner—David J. Isabella
Attorney, Agent, or Firm—Pollock, Vande Sande & Priddy

[57] ABSTRACT

A prosthesis kit comprising an elongate prosthesis body (1) and a series of modular strips (2a, 2b, 2c) of different thicknesses which are suitable for being combined with the body to constitute assemblies of different widths (Da, Db, Dc). Each of the modular strips has a longitudinally extending dovetail section edge (e.g., a dovetail tongue 20) which is suitable for interfitting in a complementary dovetail section (e.g., a groove 13) provided on a side of the elongate body, in such a manner that the interfitting dovetail sections ensure that the assembled body and strip are mutually fixed against relative sideways displacement.

2 Claims, 9 Drawing Figures

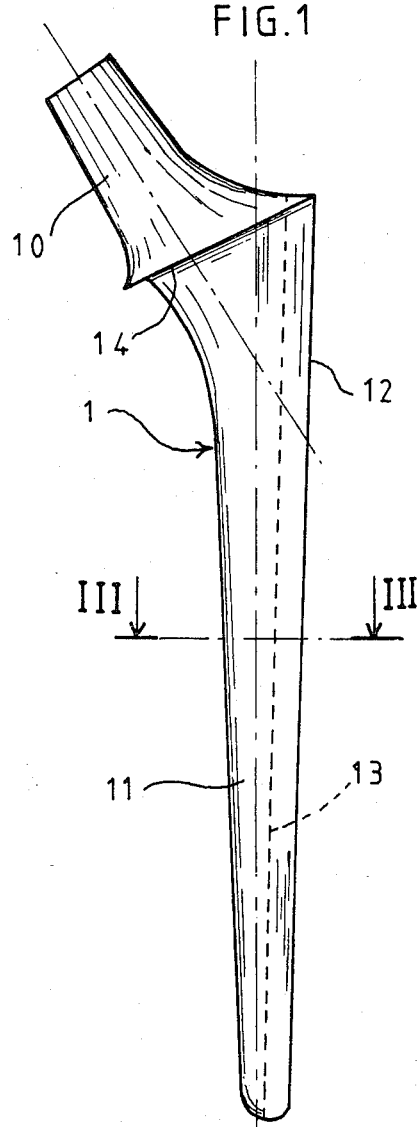
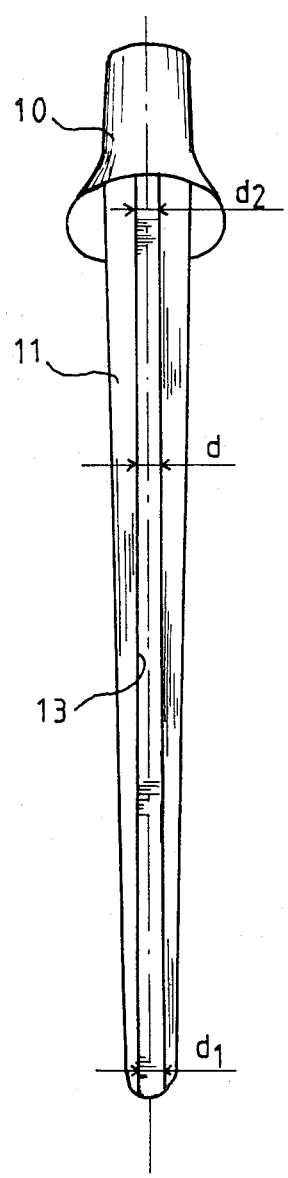
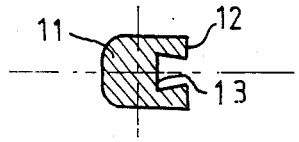

MODULAR PROSTHESIS KIT

FIELD OF THE INVENTION

The present invention relates to a prosthesis, in particular a joint prosthesis, e.g., a hip prosthesis (total or cephalic).

BACKGROUND OF THE INVENTION

Putting this type of prosthesis into place poses a problem for surgeons, since the size of the prosthesis to be used, in particular its width, depends on the size of the bone which is to receive it, and in particular on the width of the medullary canal in the bone.

It is therefore necessary for operating theaters to permanently maintain a large stock of prosthesis in a range of graduated widths. Holding and managing such a stock of expensive parts is costly, particularly since they must be stored under sterile conditions. This represents a considerable financial burden for a hospital. In addition, it is not very convenient for a surgeon to have to select the most appropriate prosthesis from such a stock whenever a prosthesis is to be used.

European Published Patent Application No. 85 147 has already proposed a hip joint prosthesis for implanting in the proximal end of the femur, which prosthesis is made up of two independent parts, namely, a main body or spatula, and a wedge-shaped side part. The side part is intended to slide in a guide profile provided on the narrow side face of the spatula.

This prior prosthesis would apparently solve the above-specified problem: in particular, the reference proposes providing a series of side parts of different thicknesses, each of which side parts may be combined with a common spatula in order to cover a range of prosthesis widths. This arrangement is essentially intended to enable the prosthesis to be placed at a specified height in the end of the femur. To this end the prosthesis is implanted in two stages:

(a) firstly, the spatula is placed in medullary canal in the desired final position; and (b) secondly, the side piece is placed against the spatula and is thrust into the femur while the spatula is held in the desired position until the outer wedge-shaped edge of the side piece comes into contact against bone tissue, and thereby locks the assembly in position by virtue of the wedging effect.

In this prior arrangement, the main body of the prosthesis and the wedge-shaped side part are thus two initially separate items which are brought together solely during prosthesis implantation. These items are never genuinely fixed relative to each other, and as a result they are difficult for the surgeon to handle both before and during implantation, and may give rise to inaccuracies. In addition, after implantation, when forces are applied to the prosthesis (and these forces may be very high, and in various different directions), there is a risk of the two parts working loose relative to each other, and thus of the prosthesis assembly working loose from the bone.

Preferred embodiments of the present invention remedy these drawbacks by providing a prosthesis of the above-described type in which handling is facilitated, both before and during implantation, and which is securely and durably retained by the bone after implantation.

SUMMARY OF THE INVENTION

The present invention provides a prosthesis kit comprising an elongate prosthesis body and a series of modular strips of different thicknesses which are suitable for being combined with said body to constitute assemblies of different widths, wherein each of said modular strips has a longitudinally extending dovetail section edge which is suitable for interfitting in a complementary dovetail section provided on a side of said elongated body, said interfitting dovetail sections ensuring that the assembled body and strip are mutually fixed against relative sideways displacement.

It will readily be understood that an operating theater can meet any requirement with a single prosthesis together with a full set of modular strips.

In addition, the selected strip is fitted to the main body prior to the prosthesis being implanted, thereby considerably facilitating manipulation of the assembly during an operation. After the assembly has been put into place, it is impossible for the two parts thereof to work loose relative to each other in a sideways direction.

Advantageously, each strip has a substantially constant thickness from end to end, thereby providing good force distribution between bone tissue and the prosthesis assembly, and hence further reducing the risks of the prosthesis working loose from the bone.

In a preferred embodiment of the invention, said dovetail sections taper slightly from end to end.

The dovetail sections can thus be wedged together while the parts are being assembled.

In this case, it is advantageous for the taper to be such that friction forces between the bone tissue and the walls of the strip as the prosthesis is being inserted into the medullary canal tend to enhance the wedging effect, since this will result in the implanted two-part prosthesis acting as a single solid item with relative displacement between the parts being prevented both laterally and longitudinally. For example, if the male or tongue dovetail section is on the modular strip, and the female or groove dovetail section is on the prosthesis body, then the wider end of both sections should to be the distal end, with the selected strip being slid into the prosthesis body from the distal end, i.e., the end which will be the bottom end when the patient is standing upright.

BRIEF DESCRIPTION OF THE DRAWINGS

An embodiment of the invention is described by way of example with reference to the accompanying drawings, in which:

FIGS. 1 and 2 are a front view and a right-hand side view respectively of the prosthesis body on its own;

FIG. 3 is a horizontal section on a plane III—III of FIG. 1;

DETAILED DESCRIPTION

Figure 4:
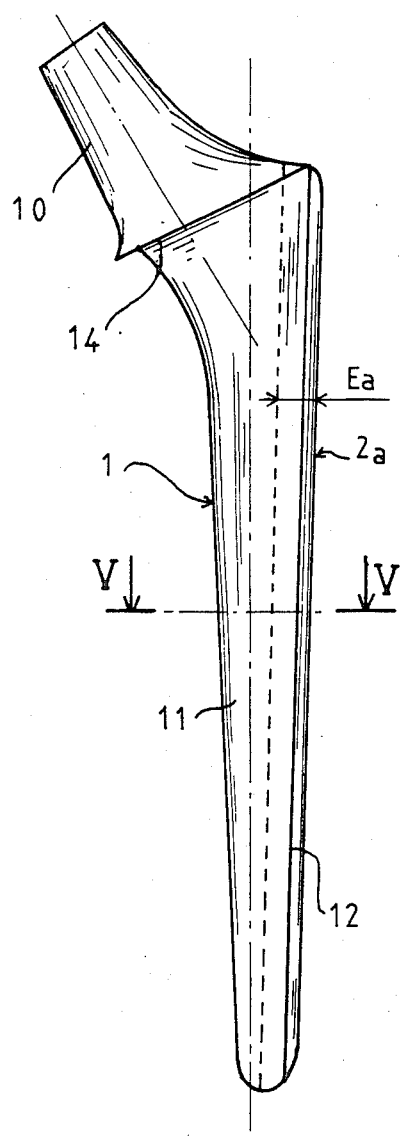
FIG. 4 is a front view of a prosthesis body to which a thin modular strip has been fixed.

The prosthesis body designated by reference 1 in FIGS. 1 to 3 is a femur prosthesis of a generally conventional type in the form of an elongate flat rod 11, a collar 14, and a Morse taper cone 10 for receiving a femur head in conventional manner.

In accordance with the invention, the outside edge 12 of the body 1 is rectilinear in shape and has a longitudinally extending dovetail-section groove 13 formed therein. The width d of this groove tapers very slightly when going from the distal end (at the bottom in FIGS. 1 and 2) towards the proximal end (at the top in the figures). For example, the width $d_1$ of the groove at its distal end may be about 4.5 mm, while its width $d_2$ at the proximal end may be about 4 mm. The groove 13 opens out at both ends of the body 1.

Figure 6:
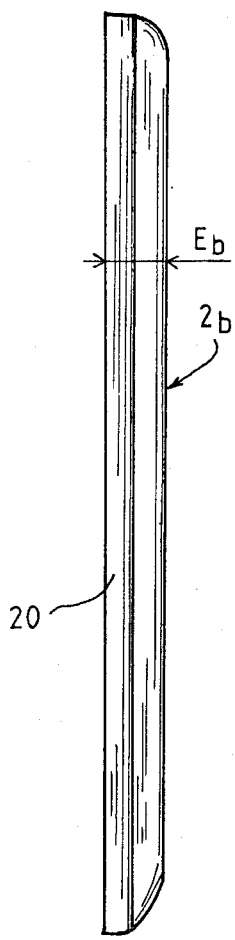
FIGS. 6 and 8 are front views of modular strips of average and of large thickness, respectively.
Figure 8:
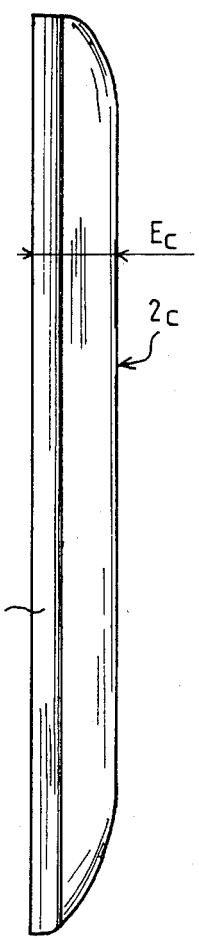
Figure 5:
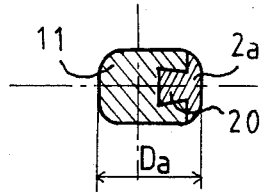
FIG. 5 is a horizontal section on a plane V—V of FIG. 4.
Figure 7:
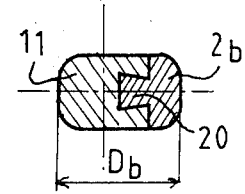
FIGS. 7 and 9 are sections analogous to FIG. 5, in which the prosthesis assembly includes the modular strip of FIGS. 6 and 8, respectively.
Figure 9:
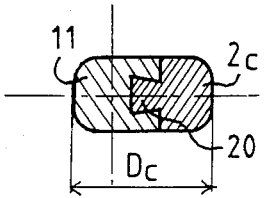

FIGS. 4, 6, and 8 show three modular strips, each of which may be fitted to the above-described prosthesis body 1.

The figures show a thin strip 2a having a thickness Ea, a medium strip 2b having a thickness Eb, and a thick strip 2c having a thickness Ec. Each of the strips is of substantially constant thickness from one end to the other. However, the outside faces of the ends themselves are curved in order to meld progressively with the corresponding ends of the prosthesis body.

Each strip 2a, 2b, 2c, . . . , in accordance with the invention has an identical inside edge 20 with a dovetail-section tongue projecting therefrom, which tongue is complementary to the groove 13 in the body 1.

FIG. 4 shows the strip 2a in place on the body 1. The strip is put into place by displacing it longitudinally upwardly relative to the body because of the upwardly tapering width d of the dovetail.

The total width of the prosthesis constituted by the prosthesis body 1 and the strip 2a is designated $D_a$ and may be 15 mm, for example, at the level represented by plane V—V.

If an average thickness strip 2b is used instead of the thin strip 2a, the resulting overall thickness $D_b$ is equal to 20 mm, and similarly if the thick strip 2c is used, the overall thickness $D_c$ is equal to 25 mm.

For the purposes of simplification, only three different modular strips are shown; however, it will readily be understood that inpractice it is desirable to provide a larger number of modular strips, for example nine strips, with thicknesses at 1 mm intervals.

The advantage of the present invention stems directly from the above explanation. Depending on the diameter of the femur and of its medullary canal in which the prosthesis is to be placed (which dimensions can be taken from X-ray pictures), the surgeon selects one of the available strips in the series, fixes the strip to the prosthesis body, and then places the prosthesis assembly in the medullary canal as though the prosthesis were a conventional unitary prosthesis.

Naturally, depending on circumstances, the prosthesis may be put into place either with cement or without cement. If no cement is used, it may be desirable to provide roughnesses such as grooves, ribs, or knurling at the top of the prosthesis body when it is initially manufactured, thereby improving prosthesis retention in the bone tissue.

The invention is not limited to the preferred embodiment described above by way of example, and numerous variants are possible.

Thus, inter alia, it is naturally possible to fix the modular strip to the prosthesis body by additional means, for example by means of a locking screw whose head is received in one or other of the two parts, and which is suitable for locking the strip and the prosthesis body in a given relative longitudinal position after the strip has been slid into engagement with the body.

In addition, the invention covers the situation where the male dovetail tongue is provided on the prosthesis body and complementary female dovetail grooves are provided on each of the modular strips.

Finally, the invention is applicable to prosthesis other than hip prosthesis, and in particular to shoulder or knee prostheses

We claim:

1. A prosthesis kit, intended for emplanting in a femur, comprising an elongated body adapted to be inserted into a prepared intramedullary cavity and having means at one end thereof for receiving a joint head, said elongated body having a generally rectilinear shape defining anterior-posterior and medial-lateral surfaces, one of said surfaces having a longitudinally extending dovetail groove formed therein, said groove having a width tapering from a distal end to a proximal end; and a series of elongated modular strips each having different thicknesses and being adapted for connection to said body to constitute assemblies of different widths, wherein each of said modular strips has a longitudinally extending dovetail tongue adapted for interfitting in a complementary dovetail groove on said body, said interfitting ensuring that said body and said modular strip are mutally fixed against sideways displacement, and wherein said taper enables said modular strip displacement, and wherein said taper enables said modular strip to be fitted to said body prior to the prosthesis being implanted such that the surgeon may impact the assembly as a unit in the cavity, whereby frictional forces between bone tissues and said unit tend to enhance wedging effect between said tapered dovetail groove and tongue during implantion.

2. A prosthesis kit according to claim 1, wherein each of said strips is of substantially constant thickness from one end to the other.

* * * * *